United States Patent [19]

de Haan et al.

[11] Patent Number: 5,662,936
[45] Date of Patent: Sep. 2, 1997

[54] SUGAR-COATED PHARMACEUTICAL DOSAGE UNIT

[75] Inventors: Pieter de Haan, Oss; Marcus Johannes Maria Deurloo, Rosmalen, both of Netherlands

[73] Assignee: Akzo Nobel, N.V., Arnhem, Netherlands

[21] Appl. No.: 360,157

[22] Filed: Dec. 20, 1994

[30] Foreign Application Priority Data

Dec. 23, 1993 [EP] European Pat. Off. ............ 93203645

[51] Int. Cl.$^6$ .................. A61K 9/34; A61K 9/36
[52] U.S. Cl. ............ 424/479; 424/481; 424/482; 424/493; 424/496; 424/497
[58] Field of Search ............. 424/401, 464, 424/474, 479, 481, 482, 493, 496, 497

[56] References Cited

U.S. PATENT DOCUMENTS

| | | | |
|---|---|---|---|
| 2,736,682 | 2/1956 | Hermelin | 167/82 |
| 3,576,663 | 4/1971 | Signorino | 117/72 |
| 3,577,512 | 5/1971 | Shepherd | 424/21 |

*Primary Examiner*—Thurman K. Page
*Assistant Examiner*—Sharon Howard
*Attorney, Agent, or Firm*—William M. Blackstone

[57] ABSTRACT

The invention relates to sugar-coated dosage units comprising a steroid having two hydrogen atoms at position 3 of the steroid skeleton, such as desogestrel, allylestrenol, ethylestrenol, or lynestrenol, to a process for the manufacture of such dosage units, and a use of sugar-coated compositions for providing stable dosage units comprising said steroid.

7 Claims, No Drawings

SUGAR-COATED PHARMACEUTICAL DOSAGE UNIT

The invention relates to sugar-coated dosage units comprising a steroid having two hydrogen atoms at position 3 of the steroid skeleton, such as desogestrel, allylestrenol, ethylestrenol, or lynestrenol, to a process for the manufacture of such dosage units, and a use of sugar-coated compositions for providing stable dosage units comprising said steroid.

Sugar-coating of compressed tablet cores and granules is one of the oldest processes known in the art. It is used to mask unpleasant tastes and odours, to protect an ingredient from decomposition as a result of exposure to air, light, or moisture, or to improve tablet appearance and increase esthetic appeal.

It has now been found that sugar-coating can be used for the solution of another problem. It was experienced that apolar active compounds, such as steroids having two hydrogen atoms at position 3 of the steroid skeleton, show a tendency to transfer out of tablets and granules comprising said apolar active compounds. This is of particular concern when the tablet cores or granules comprise very low dosages of said apolar active compounds. This is the case in tablets and granules comprising the progestagen desogestrel, allylestrenol, ethylestrenol, or lynestrenol. Tablets having desogestrel as active ingredient comprise usually 25–150 µg, and typically 25, 50, 75, 100, or 150 µg of desogestrel. Tablets having allylestrenol as active ingredient comprise usually 10–75 mg, and typically 25 mg of allylestrenol, and tablets having ethylestrenol or lynestrenol as active ingredient comprise usually 0.5–10 mg, and typically 2.0 or 2.5 mg of ethylestrenol or lynestrenol. For desogestrel, allylestrenol, ethylestrenol, or lynestrenol, which are used as active ingredient in contraceptive or HRT (hormone replacement therapy) drugs, this is not acceptable in view of their safety and reliability. A loss of for example 10% of the active substance within the shelf-life has therefore a dramatic effect on the amount of active ingredient in the tablet, and could lead to a tablet having less than the threshold amount of active ingredient to exert full activity. It is now found that sugar-coating can be used for other purposes than preventing moisture to enter the tablet or granule; it also can be used to prevent the transfer of a steroid having two hydrogen atoms at position 3 of the steroid skeleton, such as desogestrel, allylestrenol, ethylestrenol, or lynestrenol from the tablet or granule to the environment. The sugar-coated dosage unit apart from the steroid having two hydrogen atoms at position 3 of the steroid skeleton, such as desogestrel, allylestrenol, ethylestrenol, or lynestrenol can further comprise an estrogen.

Examples of estrogens include ethinyl estradiol, β-estradiol, mestranol (17-α-ethinyl estradiol 3-methylether), estrone, estradiol, estradiol valerate, and other compounds with estrogenic activity. Ethinyl estradiol and β-estradiol are the preferred estrogen.

As used herein, "transfer" includes any process in which the steroid having two hydrogen atoms at position 3 of the steroid skeleton prematurely leaves the dosage unit.

The term "dosage unit" generally refers to physically discrete units suitable as unitary dosages for humans or animals, each containing a predetermined quantity of active material (e.g. estrogen and/or desogestrel) calculated to produce the desired effect. Examples of such dosage units are tablets, granulates, powders, and pills.

Methods and compositions for making various dosage units excipients and granules are known to those skilled in the art. For example, methods and compositions for making tablets and pills are described in *Remington's* (18th edition, A. R. Gennaro Ed., Mack Publishing Co. Easton, Pa., 1990), at pages 1633 through 1665.

The concentration of steroid or steroids included in the tableting mixture, and eventually the dosage unit, will of course depend on the particular steroid's potency, its intended use, and the eventual mass of the dosage unit. The amount of asteroid or steroids used in a dosage unit will be well-known to those skilled in the art.

A tablet core or granule according to the invention comprise typically a diluent and optionally a binder. Preferably the tablet core or granulate will also include a disintegrating agent.

Diluents or "filler excipients" are agents added to dosage units to increase the granules' and resulting dosage units' bulk. The preferred diluent for use in this regard is lactose. Other diluents include mannitol, sorbitol, cellulose, xylitol, dextrose, fructose, calcium phosphate, $NaCaPO_4$, sucrose, and mixtures thereof. The diluent will typically make up from 70 to 95% by weight of the resulting steroid loaded granules.

Binders are agents used to impart cohesive properties to the granules, resulting in more physically stable dosage units, and include hydroxypropylcellulose, amylopectin, starch, povidone (polyvinylpyrrolidone), hydroxypropylmethylcellulose, gelatin, and starch based binders. The preferred binder for use with the invention is amylopectin. The binder will typically make up from 0.5 to 5% by weight of the resulting steroid loaded tablet cores or granules.

Disintegrating agent or "disintegrators" are substances or mixtures of substances added to a tablet to facilitate its breakup or disintegration after administration. Typically such agents are modified or unmodified starches, clays, cross-linked PVP, modified or unmodified celluloses, gums or algins. The presently most preferred agents are corn starch, potato starch, and wheat starch. Disintegrators will typically make up from 5 to 50%, preferably 5 to 15%, by weight of the resulting tableting mixture.

The tableting mixture may be prepared in a mixer. However, the tableting mixture can also be made in a fluidized bed granulator, and then later added to the mixer for later loading with steroid.

Mixers for use with the invention are readily commercially available and are capable of mixing or blending the dry ingredients with a solvent containing the steroid or steroids. Vacuum mixers which are closed to the outside environment are preferred for workers' safety and environmental reasons since the solvent is not released into the atmosphere, and can be collected for re-use.

The "wet" portion added to the carrier will preferably consist of the steroid or steroids, an anti-oxidant, and a lubricant all dissolved or suspended in a solvent.

Lubricants are agents which improve the rate of flow of the tablet granulation, prevent adhesion of the tablet material to the surface of dies and punches, reduce interparticle friction, and facilitate the ejection of the tablets from the die cavity. Commonly used lubricants are talc, long chain fatty acids, magnesium stearate, stearic acid, calcium stearate, polyethylene glycol, palmitic acid, and hydrogenated vegetable oils. The lubricant will typically make up from 0.25 to 3% by weight of the resulting granules.

Solvents for use with the invention are preferably those having a sufficiently low boiling point at the pressures attainable in the vacuum mixer to evaporate off during the process. These include acetone, dichloromethane, ethanol, methanol, isopropanol, and mixtures thereof. When miscible these organic solvents may be mixed with water. The binder need not be very soluble in the solvent.

A sufficient amount of solvent will be used to dissolve the steroid or steroids, and when present the lubricant and anti-oxidant, and to wet the carrier without impairing the flow properties. Thus the amount of solvent used in the process will depend upon the potency and solubility characteristics of the particular steroid or steroids in the particular solvent, the solubility of the other components in the solvent, and the size of the batch of carrier to be wetted. Solvents will typically make up from 5 to 20% by weight of the mixture of solution and carrier.

After removal of the solvent, a flow enhancer is preferably mixed with the drug loaded tableting mixture. The flow enhancer (e.g. talc or colloidal silicon dioxide) acts to prevent the tableting mixture from clumping. Flow enhancers will typically make up from 0.1 to 3% by weight of the resulting mixture.

The use of other conventional additives or "further excipients", e.g. colorants, stabilizers or anti-oxidants, is contemplated. Stabilizers such as EDTA, polyethylene glycol (PEG), and butylated hydroxytoluene (BHT), may also be included if desired, although it is not required. The presently most preferred anti-oxidant for use with the invention is dl-$\alpha$-tocopherol. Other medicinal agents (e.g. $\beta$-estradiol) may also be included in the formulation.

The tableting mixture may also be obtained by a solvent-free process. The active ingredients may be dry-mixed, for instance with spray-dried lactose, to obtain a tableting mixture free of trace amounts of solvent. Suitable processes for dry-mixing desogestrel are described inter alia in U.S. Pat. No. 3,432,507 and EP-A-503,521, which are included by reference.

The tableting mixture may then be tabletted by means well-known to those skilled in the art.

The tablet cores or granules may then be subjected to a process for the preparation of sugar-coated tablet cores or granules comprising a steroid having two hydrogen atoms at position 3 of the steroid skeleton, preferably being desogestrel, allylestrenol, ethylestrenol, or lynestrenol, characterized by optional sealing, followed by subcoating, syruping, finishing and optionally polishing of the sugar-coated tablet core or granule. Sugar-coating processes are, for example, described in Remington's, pages 1667–1668.

The sugar-coating operation should be carried out in a facility in which temperature, moisture, and dust can be closely controlled. Large coating pans, preferably of stainless steel and usually about 1 m in diameter and 75 cm in depth, are used. Many other variations and sizes are also workable. In particular, the Accela-Cota and the Pellegrini pans represent a suitable pan design.

For optimum results the tablets should have an optimum convexity, which must represent a compromise between a curve sufficient to minimize problems with edge coverage and one not great enough to create problems in covering high spots at the crown of the curvature. It is desirable for the tablet cores to disintegrate rapidly once the coating is dissolved in vivo. Disintegrating agents, such as starch, can facilitate dissolution.

A seal coat is applied directly over the tablet cores or granules. Many substances can be used as the sealing agent, among which cellulose acetate phthalate, zein, shellac, copolymer of dimethylaminoethyl methacrylate and methacrylic acid ester (Eudragit®), and specific resins. Dusting compounds as asbestos-free talc and terra alba can be added to prevent the tablet cores and granules from adhering to one another and to the pan during the seal coat. At least two seal coats are usually necessary, but as many of six or more seal coats can be applied.

Subcoating can be achieved by application of a gum-based solution, for example an aqueous gelatin/gum acacia/sucrose solution, to the sealed cores. The procedure of application of gum solution, spreading, dusting and drying is continued until the requisite build-up has been achieved.

Syruping involves the application of a syrup concentrate. This step builds up a solid colour. It may be necessary first to apply a smoothing syrup layer, by the application of a simple syrup solution (approx. 60–70% sugar solids). This syrup solution may contain a low percentage (approx. 1–5%) of titanium dioxide as an opacifier. The completion of the sugar-coating process involves the multiple application of syrup solution (approx. 60–70% sugar solids) containing the requisite colouring material. At this stage also flavours can be added. The dyes and flavours must be of the type that are acceptable for pharmaceutical use. The sugar-coated dosage units may be polished to achieve a final gloss. Polishing is achieved by applying mixtures of waxes (e.g. beeswax, carnauba wax, candelila wax, or hard paraffin wax) in a polishing pan. The wax mixtures may be applied as powders or as dispersions in various solvents.

The invention is further illustrated by the following examples.

EXAMPLE 1

A quantity of 5 kg of the tablet cores of Example 2 (see below) was loaded in a sugar-coating pan and heated with hot air of 50° C. To the rotating tablet bed were added in quantities of approximately 75 ml, 750 ml of a solution of 75 g of the copolymer of dimethylaminoethyl methacrylate and methacrylic acid ester in 2-propanol. After each addition a spoonful of talc was added to prevent sticking of the tablet cores. Subsequently the tablet cores were unloaded and dried at 30° C. overnight. After drying the tablet cores were again loaded in the sugar-coating pan and heated with hot air of 50° C. To the tablet bed were added in quantities of approximately 75 ml, 225 ml of a solution of 163 g of sucrose, 14.8 g of acacia, 6.3 g of glucose sirup and 60.4 g of cornstarch in water. After each addition a spoonful of a mixture of colloidal silicon dioxide and talc was added. Then the tablet cores were coated with 2000 ml of a suspension containing 1338 g of sucrose, 123 g of arabinose, 152 g of calcium carbonate, 47 g of titanium dioxide, 60 g of chinolin lake E 104 and 18 g of polyvinylpyrrolidone in water. Each time a quantity of approximately 75 ml was added to the tablet bed, followed by a spoonful of talc. In between the tablet cores were unloaded twice and dried at 30° C. overnight.

Finally the coated tablet cores were waxed with 5 g of high-wax. During the coating process, in total 1350 g of talc and 25 g of aerosil were used. The coated tablet cores thus obtained have a calculated composition of the sugar-coating as indicated in the following table:

|  | quantity in mg | |
| --- | --- | --- |
| INGREDIENT | 60 mg tablet | 100 mg tablet |
| SEAL COAT | | |
| dimethylaminoethyl methacrylate and methacrylic acid ester copolymer | 0.90 | 1.50 |

-continued

| INGREDIENT | quantity in mg | |
|---|---|---|
| | 60 mg tablet | 100 mg tablet |
| SUB COAT | | |
| sucrose | 1.95 | 3.25 |
| acacia | 0.18 | 0.30 |
| glucose syrup | 0.08 | 0.13 |
| talc | 3.62 | 6.04 |
| corn-starch | 0.72 | 1.21 |
| colloidal silicon dioxide | 0.30 | 0.50 |
| SUGAR COAT | | |
| sucrose | 16.06 | 26.76 |
| acacia | 1.48 | 2.46 |
| talc | 12.57 | 20.95 |
| calcium carbonate | 1.83 | 3.05 |
| titanium dioxide | 0.56 | 0.94 |
| chinolin lake E 104 | 0.72 | 1.20 |
| polyvinylpyrrolidone | 0.22 | 0.36 |
| high-wax | 0.06 | 0.11 |
| total | 41.25 | 68.76 |

EXAMPLE 2

Tablets of the following composition were prepared:

| desogestrel (micronized) | 150 µg |
|---|---|
| EE (micronized) | 30 µg |
| Na starch glycolate | 1.2 mg |
| Mg Stearate | 0.3 mg |
| spray-dried lactose (Pharmatose DCL-11) qsad | 60.0 mg |

These tablets were made by first dry mixing desogestrel and EE (ethinyl estradiol) with proportionate quantities of spray-dried lactose. The other ingredients were then also mixed into the mixture. The mixture was then tabletted by direct compression (tablet "A"). Part of the tablets was sugar-coated according to the procedure of Example I (tablet "B").

The tablets were stored for 72 hours at a pressure of 150 mbar, at a temperature of 70° C., and the transfer of drug from the tablet were measured, with the following results:

Transfer from dosage unit:

| Subject | percentage of transferred desogestrel |
|---|---|
| Tablet "B" | 0.05* |
| Tablet "A" | 13 |

*detection limit

EXAMPLE 3

Tablets of the following composition were prepared:

| desogestrel | 150 µg |
|---|---|
| EE | 30 µg |
| dl-α-tocopherol | 80 µg |
| Mg stearate | 0.5 mg |
| potato starch | 10.10 mg |
| amylopectin | 1.790 mg |
| lactose | 87.35 mg |

The bowl of a fluid bed granulator was loaded with 5421 g of lactose and 607 g of potato starch. A mucilage of 107 g of amylopectin in water was sprayed onto the fluidized bed. After drying, the granulate was unloaded and screened and then loaded into a vacuum mixer. A solution containing 9.000 g of desogestrel, 1.800 g of ethinyl estradiol and 4.800 g of dl-α-tocopherol in 0.28 l of acetone was homogeneously distributed over the granulate. After evaporation of the solvent, 30 g of magnesium stearate was admixed to the granulate. The granulate was finally compressed into tablets with a diameter of 6 mm and a mass of 100 mg (Tablet "C").

A quantity of 5 kg of Tablet "C" was sugar-coated according to the procedure of Example I, giving Tablet "D".

The tablets were stored for 72 hours at a pressure of 150 mbar, at a temperature of 70° C., and the transfer of drug from the tablet were measured, with the following results:

Transfer from dosage unit:

| Subject | percentage of transferred desogestrel |
|---|---|
| Tablet "D" | 0.1 |
| Tablet "C" | 18.7 |

We claim:

1. A process for inhibiting transfer of a steroid from a tablet core or a granule that comprises a steroid having two hydrogen atoms at position 3 of the steroid skeleton, comprising subcoating, syruping and finishing the tablet core or granule whereby it becomes sugar-coated.

2. A sugar-coated dosage unit having a core comprising a steroid having two hydrogen atoms at position 3 of the steroid skeleton encapsuled within a sugar coating, wherein the sugar coating comprises subcoating and syruping layers.

3. The sugar-coated dosage unit of claim 2, comprising at least one steroid selected from the group consisting of desogestrel, allylestrenol, ethylestrenol and lynestrenol.

4. The sugar-coated dosage unit of claim 2, wherein the composition further comprises an estrogen.

5. The sugar-coated dosage unit of claim 2, wherein the dosage unit is a tablet core or a granule.

6. The sugar-coated dosage unit of claim 2, wherein the composition comprises desogestrel.

7. The sugar-coated dosage unit of claim 4, wherein the estrogen is ethinyl estradiol or β-estradiol.

* * * * *